US006381491B1

(12) United States Patent
Maile et al.

(10) Patent No.: US 6,381,491 B1
(45) Date of Patent: Apr. 30, 2002

(54) DIGITALLY TRIMMABLE RESISTOR FOR BANDGAP VOLTAGE REFERENCE

(75) Inventors: Keith R. Maile, New Brighton; Terrence L. Marshall, Minneapolis; William J. Linder, Golden Valley, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/642,287

(22) Filed: Aug. 18, 2000

(51) Int. Cl.[7] .............................. A61N 1/00; G05F 1/10
(52) U.S. Cl. ........................................... 607/2; 327/539
(58) Field of Search ......................... 607/2, 1; 323/313, 323/314, 315, 316, 907; 327/539

(56) References Cited

U.S. PATENT DOCUMENTS 4,733,160 A 3/1988 Draxelmayr ................ 323/314
5,670,868 A 9/1997 Moriguchi et al. ......... 323/313
5,841,270 A 11/1998 Do et al. .................... 323/314
5,929,616 A 7/1999 Perraud et al. ............. 323/274
6,034,391 A 3/2000 Tobita ........................ 257/306
6,046,578 A 4/2000 Feldtkeller .................. 323/314
6,124,754 A 9/2000 Afghani ...................... 327/538
6,150,871 A 11/2000 Yee ............................ 327/538
6,172,555 B1 1/2001 Gusinov ..................... 327/539
6,181,196 B1 1/2001 Nguyen ...................... 327/539

*Primary Examiner*—Scott M. Getzow
(74) *Attorney, Agent, or Firm*—Schwegman, Lundberg, Woessner & Kluth, P.A.

(57) ABSTRACT

A bandgap voltage reference circuit implemented on an integrated circuit chip in which a proportional-to-temperature current is controlled by a current controlling resistor and converted to a voltage by a voltage controlling resistor, with either or both of the resistors being an integrated on-chip digitally trimmable resistor. The reference circuit is particularly suitable for application to circuitry used in implantable medical devices where off-chip resistors provide a channel by which noise can interfere with the operation of the circuit. The on-chip digitally trimmable resistor is implemented in accordance with the invention by a programmable switch matrix connected to a resistor network.

20 Claims, 3 Drawing Sheets

DIGITALLY TRIMMABLE RESISTOR FOR BANDGAP VOLTAGE REFERENCE

FIELD OF THE INVENTION

This invention pertains to apparatus and methods for generating reference voltages in electronic circuits. In particular, the invention relates to integrated circuit implementations of voltage reference circuits that are applicable to implantable medical devices such as pacemakers and cardioverter/defibrillators.

BACKGROUND

Implantable medical devices, such as cardiac pacemakers and cardioverter/defibrillators, employ electronic control circuitry to enable the device to appropriately respond to sensed cardiac events and lapsed time intervals. A necessary component of such circuitry is a circuit for producing a fixed reference voltage. One type of circuit that is commonly used for providing a fixed reference voltage is the so-called bandgap voltage reference. Unlike other voltage references, such as Zener diodes, this circuit generates a reference voltage that is independent of temperature. Basically, as will be described in more detail below, a bandgap voltage reference generates a temperature independent voltage by adding together two voltages with opposite temperature coefficients. The circuit utilizes a current source with a positive temperature coefficient, referred to herein as a proportional-to-absolute temperature (PTAT) current source, to generate one of the voltages by flowing the current through a voltage converting resistor. In order for the circuit to perform properly and generate a temperature independent reference voltage, the voltage reference circuit must be tuned so that the PTAT current source delivers a precise amount of current across a precise resistance. The current magnitude that the source must deliver and the voltage converting resistance value may vary, however, due to amplifier offset, current source mismatch, and variation in junction characteristics. Since these parameters cannot be determined until the rest of the circuit is manufactured, the usual method of tuning the reference circuit is to trim (i.e., adjust) a current controlling resistor and/or the voltage converting resistor after the circuit is manufactured until the desired current level and reference voltage is obtained.

The method described above for tuning the reference circuit presents a particular problem, however, with respect to implantable medical devices. In order to reduce both space and power requirements, the circuitry of such devices is fabricated on integrated circuit (IC) chips whenever possible. The components of the bandgap voltage reference circuit can similarly be placed on an IC chip with the exception of the trimmable current controlling resistor of the PTAT current source and the voltage converting resistor. This is because most resistive elements on an IC chip are diffused resistors that cannot be adjusted after they are fabricated. Prior manufacturing methods have therefore located the current controlling resistor of the PTAT current source and the voltage converting resistor off-chip where they can be laser trimmed after the circuit is manufactured. Locating these resistors off-chip, however, provide noise channels that can adversely affect the operation of the bandgap voltage reference circuit. Due to the very low output current and non-linear nature of the PTAT circuit, it is extremely sensitive to noise from various sources (e.g., external electromagnetic interference, capacitively coupled current) that enter the circuit through the connections of the external trimmable resistors. This has necessitated the use of expensive and cumbersome EMI shielding in implantable medical devices to overcome the problem. It is a primary objective of the present invention to provide a trimmable resistor for a reference circuit that does not increase its noise susceptibility.

SUMMARY OF THE INVENTION

In accordance with the invention, a digitally trimmable resistor is provided as a current controlling resistor and/or a voltage converting resistor as part of a bandgap voltage reference circuit. The trimmable resistors, along with other components of the bandgap voltage reference circuit, may then be fabricated on an integrated circuit chip. Fabricating a resistor as an on-chip digitally trimmable resistor allows it to be trimmed after manufacture and greatly improves the noise immunity of the reference circuit as compared with an off-chip resistor. Such a bandgap voltage reference circuit fabricated on an integrated circuit chip includes a current source for generating an output current with a positive temperature coefficient and an on-chip digitally trimmable current controlling resistor for determining the magnitude of the output current and/or an on-chip digitally trimmable voltage converting resistor. The circuit further includes a p-n junction voltage source which has a negative temperature coefficient, where the negative coefficient voltage is added to a positive coefficient voltage derived from the output current of the current source to produce a reference voltage.

In one embodiment, an on-chip digitally trimmable resistor is implemented as a resistor network connected to a switch array. The resistor network comprises a plurality of individual series connected resistors, with each resistor connected in parallel with a switch of the switch array. A switch closure therefore shorts the current path around the resistor to which the switch is connected and electrically removes the resistor from the network. The state of the individual switches of the array thus determines the total ohmic resistance of the resistor network. By implementing the switch array as, for example, an array of MOSFET transistors, the switch states can be determined by the gate voltages applied to each individual resistor. The digitally trimmable resistor may then be trimmed so as to result in the desired output current from the current source and/or desired reference voltage after manufacture of the integrated circuit chip. In a presently preferred embodiment, the gate voltages of the MOSFETs are controlled by the bit lines of an electrically erasable programmable read-only memory (EEPROM). The ohmic value of the digitally trimmable resistor is then determined by the values programmed into the memory locations of the EEPROM.

DETAILED DESCRIPTION OF THE INVENTION

Figure 1:
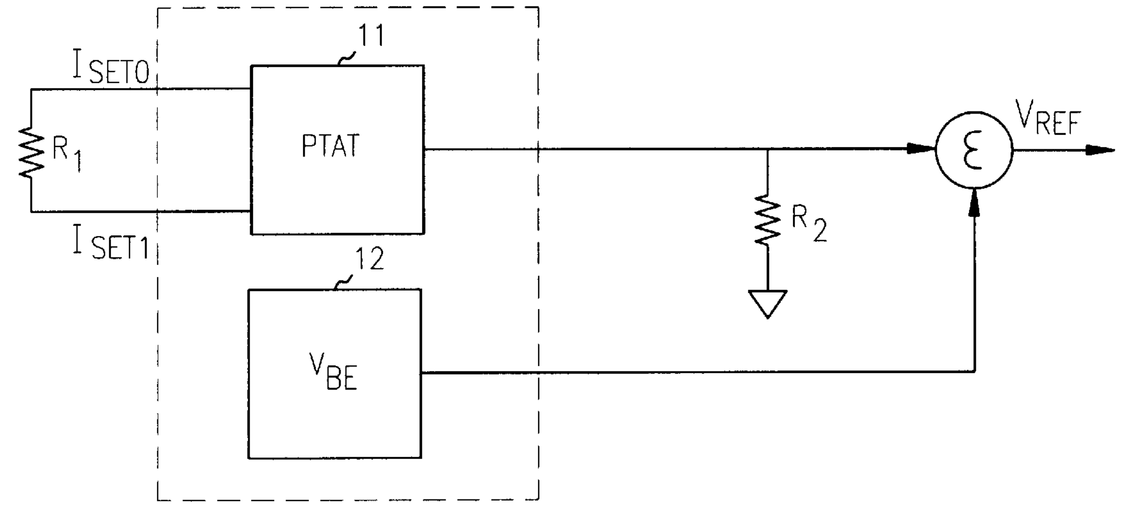
FIG. 1 is a block diagram of a bandgap voltage reference circuit.

As noted above, a bandgap voltage reference circuit generates a fixed reference voltage with no temperature dependency by adding a voltage with a positive temperature coefficient to a voltage with a negative temperature coefficient. FIG. 1 shows a block diagram of the components of an integrated circuit bandgap voltage reference in prior implementations. The components within the box labeled IC are located on the integrated circuit chip. A proportional-to-absolute-temperature (PTAT) current source 11 generates a current with a positive temperature coefficient, with the magnitude of the current controlled by the value of an off-chip resistor $R_1$ connected to the current source by terminals ISET0 and ISET1. The PTAT current is then converted into a voltage by an off-chip resistor $R_2$ connected via terminals VSET0 and VSET1. The voltage across resistor $R_2$ is then summed with a negative temperature coefficient voltage generated by $V_{BE}$ voltage source 12, normally obtained from the base-to-emitter voltage drop of a transistor. The result of the summed voltages is the temperature independent reference voltage VREF.

Figure 2A:
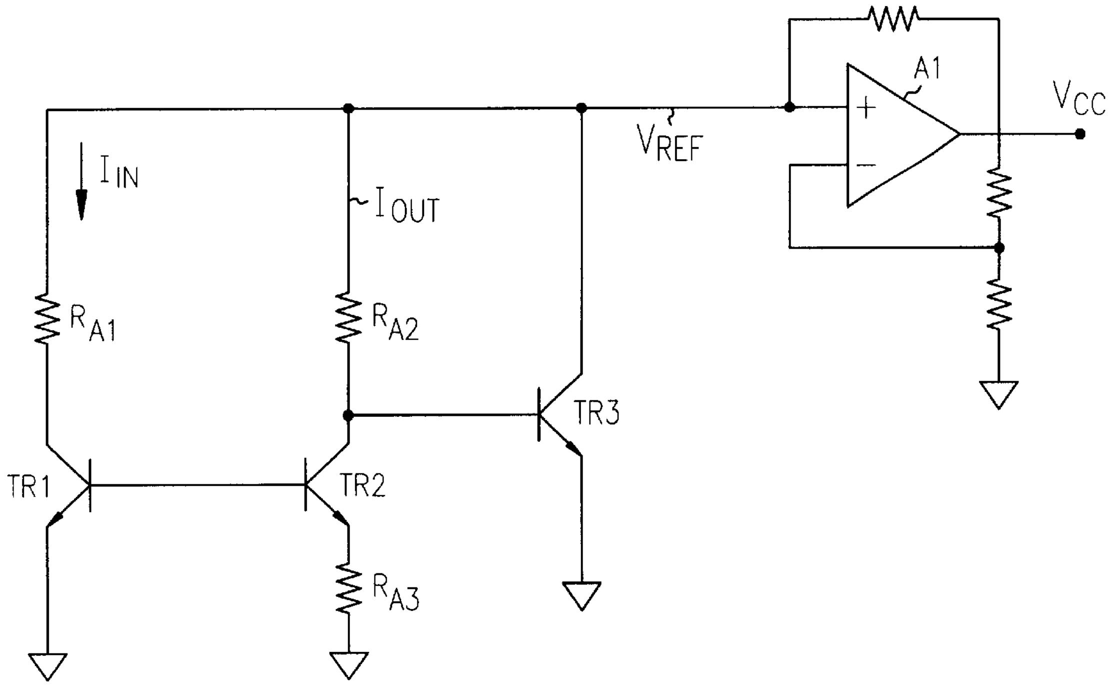
FIGS. 2A and 2B show in more detail exemplary implementations of bandgap voltage reference circuits.

FIG. 2A shows in more detail an exemplary common implementation of a bandgap voltage reference circuit. A PTAT current source is implemented as a current mirror made up of two transistors TR1 and TR2 operating at different emitter current densities. The collector currents of TR1 and TR2 are the input current $I_{in}$ and the mirrored output current $I_{out}$, respectively. Due to emitter resistor $R_{A3}$, the output current $I_{out}$ is some constant fraction of the input current $I_{in}$. The magnitude of the input current is controlled by the value of the collector resistor $R_{A1}$ of transistor TR1 which, in turn, determines the magnitude of the output current $I_{out}$ through the operation of the current mirror. Due to the current density ratios of the current mirror, the mirrored current $I_{out}$ has a positive temperature coefficient and is converted to a voltage with similar temperature dependence by resistor $R_{c2}$. The voltage dropped across $R_{A2}$ is then added to the base-to-emitter voltage $V_{BE}$ of transistor TR3, which has a negative temperature coefficient, to result in the voltage VREF. In this particular circuit, VREF is fed to a feedback amplifier A1 and is also used to generate the input current for the current mirror.

Figure 2B:
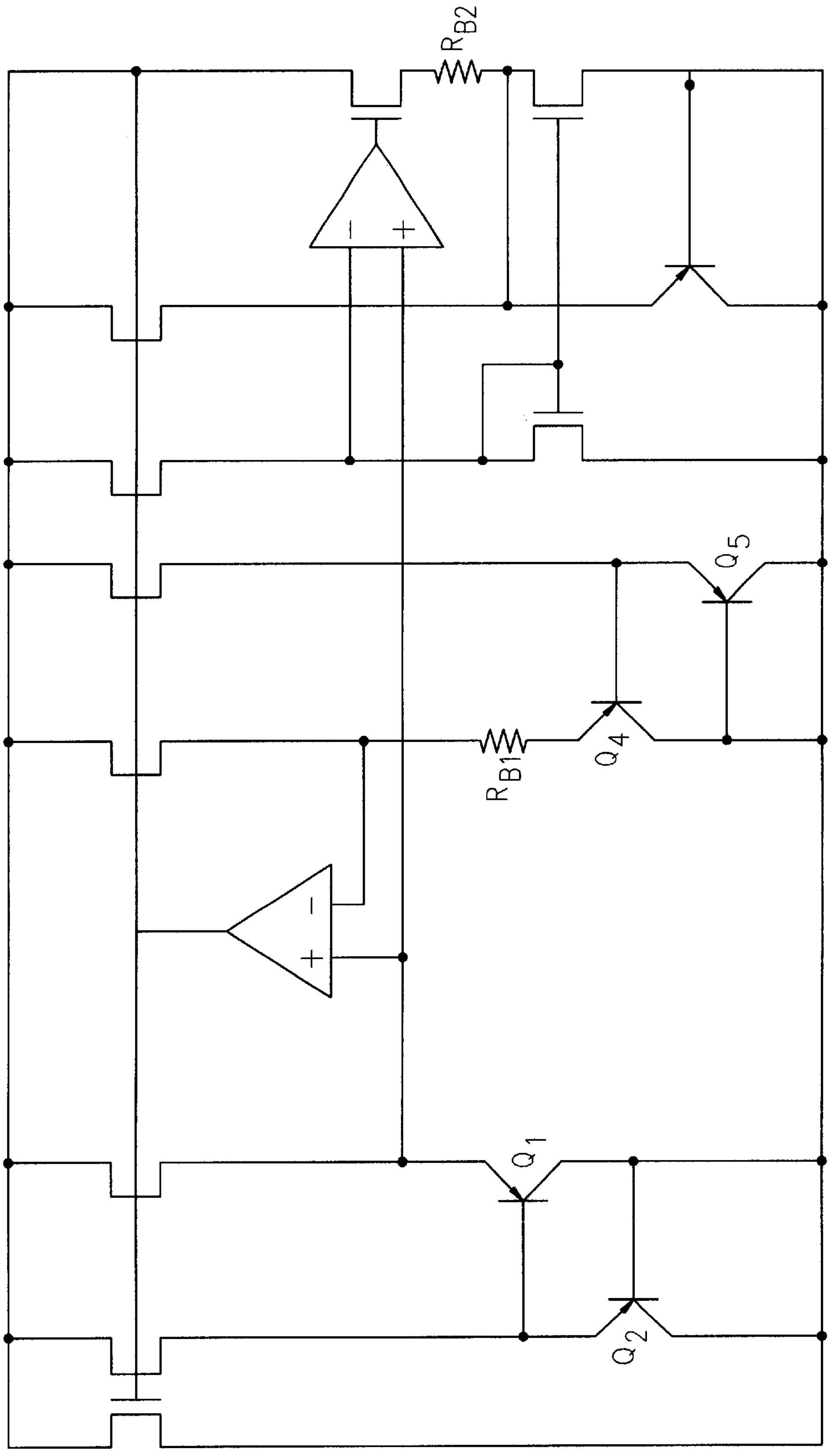

FIG. 2B shows another exemplary bandgap voltage reference circuit. A PTAT current source is provided by generating a fixed ratio of current densities through two sets of transistors Q1, Q2 and Q4, Q5. The voltage difference due to the different current densities is applied across resistor $R_{B1}$. The value of the PTAT current is nominally given by:

$$\text{PTAT}=2*V_T*1n(\text{current ratio})/R_{B1}$$

where $V_T$=0.0267 volts at 37 degrees C and is proportional to absolute temperature. A voltage reference VREF is generated by summing a base-to-emitter voltage $V_{BE}$ with the voltage across resistor $R_{B2}$ through which the PTAT current is flowing. Many different bandgap voltage reference circuits have been designed, but virtually all work basically by summing a $V_{BE}$ voltage with a voltage generated by a pair of transistors operating at different current densities.

The magnitude of the output current of the PTAT current source (i.e., the mirrored current $I_{out}$ in FIG. 2) is dependent upon the input current $I_{in}$ which is determined by the ohmic value of the input current controlling resistor (i.e., $R_1$ in FIG. 1, $R_{A1}$ in FIG. 2A, or $R_{B1}$ in FIG. 2B). This current is converted to a voltage by a voltage converting resistor (i.e., $R_2$ in FIG. 1, $R_{A2}$ in FIG. 2A, or $R_{B2}$ in FIG. 2B). One or both of these resistors must therefore be trimmed to values to produce a voltage that, when added to a $V_{BE}$ voltage, results in a temperature independent reference voltage. In this circuit, the resistors are typically trimmed to result in an output current of between 25 nanoamps and 1 microamp and a reference voltage of 1.25 volts. (In bandgap voltage reference circuits, the reference voltage corresponds to the bandgap energy of silicon, hence the name.) This requires that the output current (or reference voltage) must be monitored while the resistor is trimmed until the appropriate value is obtained. Resistance elements are usually fabricated on integrated circuit chips by diffusion processes, however, and such diffused resistors cannot be adjusted after they are fabricated. As noted earlier, prior methods have dealt with this issue by locating a resistor external to the integrated circuit chip that can be trimmed (usually by laser) during the manufacturing process, resulting in increased susceptibility of the reference circuit to noise.

Figure 3:
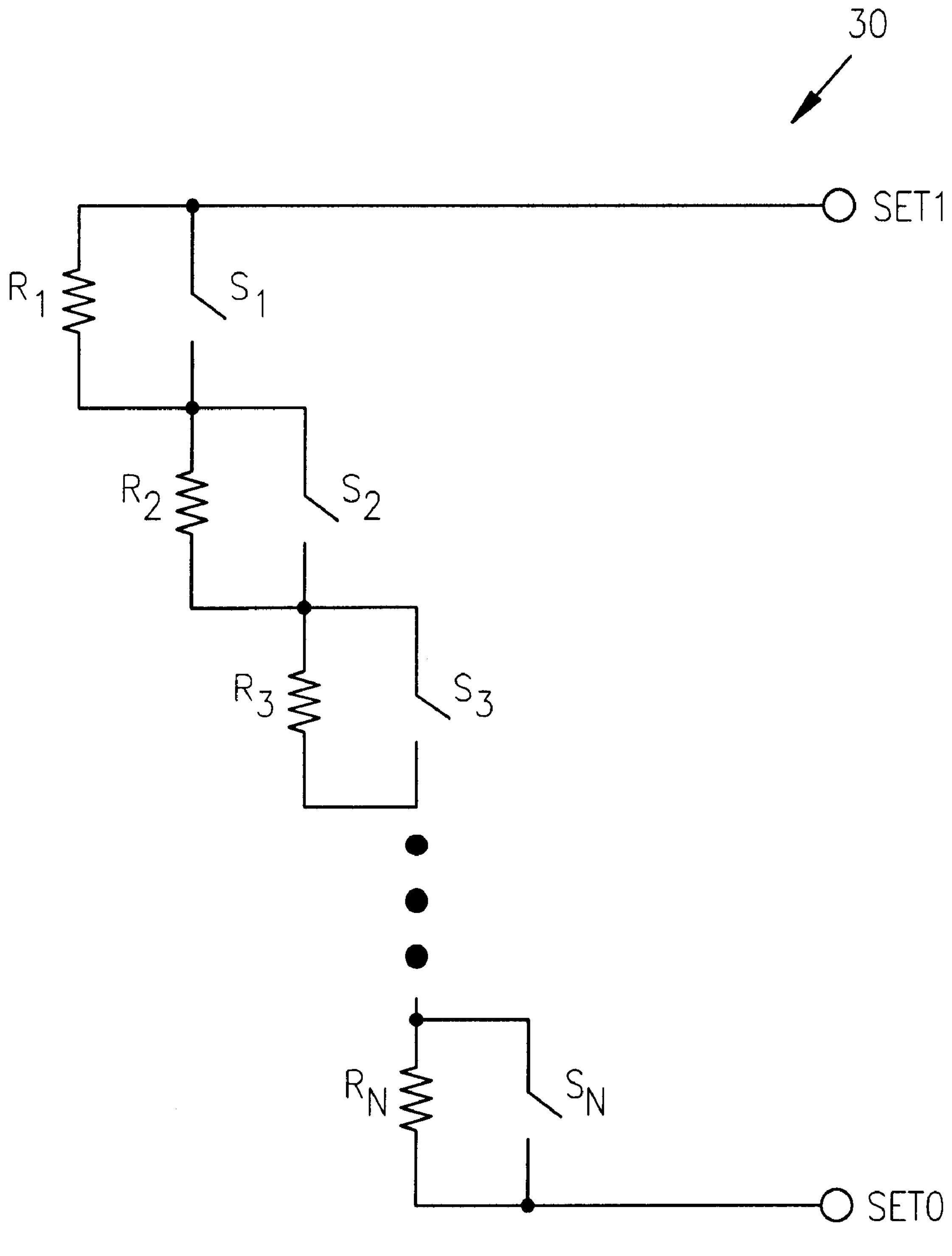
FIG. 3 is a schematic of a digitally trimmable resistor in accordance with the invention.

In accordance with the present invention, on the other hand, the input current controlling resistor and/or voltage converting resistor are implemented as digitally trimmable resistors made up of a resistor network and a switch array. FIG. 3 shows a schematic of a switch array 30 and resistor network RN for implementing the on-chip digitally trimmable resistor. The array is made up of a plurality of switches $S_1$ through $S_N$ connected in series between two terminals SET1 and SET2. The terminals would correspond to either ISET1 and ISET0 or to VSET1 and VSET0 in FIG. 1. A resistor network RN comprises a plurality of individual resistors $R_1$ through $R_N$, each of which is connected in parallel with one of the switches $S_1$ through $S_N$, respectively. The total resistance between the terminals SET1 and SET0 is thus the sum of those resistors of the network RN that are connected in parallel with an open switch of the array 30. By selectively closing the array switches, the total resistance may be adjusted to a desired value. In an exemplary embodiment, the individual resistors $R_1$ through $R_N$ have values defined with respect to a constant K as $(K*2^1)$ through $(K*2^N)$, respectively. By making the resistor values proportional to successive negative powers of two, the total conversion resistance can range from 0 to $K-(K*2^N)$ in increments of $(K*2^N)$. Both the switch array 30 and resistor network RN can be fabricated on an integrated circuit chip, the former as an array of MOSFET transistors. The current controlling resistance is then defined by the voltages applied to the gates of the MOSFETs. In a presently preferred embodiment, the states of the on-chip switch array are controlled by the bit lines of an electrically erasable programmable read-only memory (EEPROM) when a specified memory location is addressed. The total resistance of the digitally trimmable resistor is then specified by programming the EEPROM so that a value corresponding to the desired state of the switch array is stored in the addressed memory location.

Since the object of a bandgap voltage reference circuit is to generate a temperature independent voltage, it is desirable for the resistance values of the trimmable resistors described above to also be temperature independent. There are a number of ways to fabricate a temperature independent resistor on an integrated circuit chip such as constructing each individual resistor (i.e., each of the resistors making up the resistor network RN in FIG. 3) as a combination of one component with a positive temperature coefficient and another component with a negative temperature coefficient. In a presently preferred embodiment, the positive temperature coefficient component is an N-well resistor (i.e., made from lightly doped N-type silicon), and the negative temperature coefficient component is a polyresistor (made from polysilicon).

A bandgap reference circuit as described above can thus be fabricated on an integrated circuit chip with an on-chip adjustable input current controlling resistor. After fabrication of the circuit, the current controlling resistor is trimmed by monitoring the current from the PTAT current source (e.g., with a current mirror) and programming the EEPROM with the value that results in the desired current. Similarly, the voltage converting resistor is trimmed by monitoring the reference voltage produced by the circuit. In this way, the necessity of locating the resistors external to the integrated circuit chip is avoided, and the noise susceptibility of the bandgap voltage reference circuit is greatly reduced.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A bandgap voltage reference circuit fabricated on an integrated circuit chip, comprising:

a current source for generating an output current with a positive temperature coefficient, wherein the magnitude of the output current is controlled by a current controlling resistor;

a voltage source with a negative temperature coefficient, wherein the negative coefficient voltage is added to a positive coefficient voltage derived from the output current of the current source to produce a reference voltage; and, an on-chip digitally trimmable current controlling resistor for the current source, enabling the output current to be adjusted after fabrication of the circuit.

2. The circuit of claim 1 wherein the digitally trimmable resistor comprises a network of resistors connected to an array of switches whose states determines the resistance of the network.

3. The circuit of claim 2 wherein the resistor network comprises a plurality of individual series connected resistors, with each resistor connected in parallel with a switch of the switch array.

4. The circuit of claim 3 wherein the switch array comprises an array of MOSFET transistors whose switching states are determined by the gate voltages applied thereto.

5. The circuit of claim 4 further comprising a programmable read-only memory for controlling the gate voltages with bit lines of the read-only memory.

6. The circuit of claim 2 wherein the individual resistors making up the resistor network are constructed as a combination of one component with a positive temperature coefficient and another component with a negative temperature coefficient.

7. The circuit of claim 2 wherein the current source is a proportional-to-absolute-temperature current source.

8. The circuit of claim 2 wherein the digitally trimmable resistor is trimmed by monitoring the output current of the current source while changing the states of the switches until a desired value is reached.

9. The circuit of claim 2 wherein the negative coefficient voltage is generated by a base-to-emitter junction of a transistor.

10. The circuit of claim 2 further comprising an on-chip digitally trimmable voltage converting resistor for converting the output current of the current source to a voltage for adding to the negative coefficient voltage.

11. An implantable medical device having control circuitry incorporating a bandgap voltage reference circuit as set forth in claim 10.

12. The implantable medical device of claim 11 wherein the digitally trimmable resistor comprises a network of resistors connected to an array of switches whose states determines the resistance of the network.

13. The implantable medical device of claim 12 wherein the resistor network comprises a plurality of individual series connected resistors, with each resistor connected in parallel with a switch of the switch array.

14. The implantable medical device of claim 13 wherein the switch array comprises an array of MOSFET transistors whose switching states are determined by the gate voltages applied thereto and further comprising a programmable read-only memory for controlling the gate voltages with bit lines of the read-only memory.

15. A bandgap voltage reference circuit fabricated on an integrated circuit chip, comprising:

a current source for generating an output current with a positive temperature coefficient, wherein the magnitude of the output current is controlled by a current controlling resistor;

a voltage source with a negative temperature coefficient, wherein the negative coefficient voltage is added to a positive coefficient voltage derived from the output current of the current source to produce a reference voltage; and, an on-chip digitally trimmable voltage converting resistor for converting the output current of the current source to a voltage for adding to the negative coefficient voltage, enabling the reference voltage to be adjusted after fabrication of the circuit.

16. The circuit of claim 15 wherein the digitally trimmable resistor comprises a network of resistors connected to an array of switches whose states determines the resistance of the network.

17. The circuit of claim 16 wherein the resistor network comprises a plurality of individual series connected resistors, with each resistor connected in parallel with a switch of the switch array.

18. The circuit of claim 17 wherein the switch array comprises an array of MOSFET transistors whose switching states are determined by the gate voltages applied thereto.

19. The circuit of claim 18 further comprising a programmable read-only memory for controlling the gate voltages with bit lines of the read-only memory.

20. The circuit of claim 16 wherein the individual resistors making up the resistor network are constructed as a combination of one component with a positive temperature coefficient and another component with a negative temperature coefficient.

* * * * *